United States Patent [19]

Jones et al.

[11] Patent Number: 5,140,527
[45] Date of Patent: Aug. 18, 1992

[54] METHOD FOR THE DETERMINATION OF THE IONIC CONTENT OF DRILLING MUD

[75] Inventors: Timothy Jones; Trevor Hughes, both of Cambridge; Philip Fletcher, Hardwick, all of England

[73] Assignee: Schlumberger Technology Corporation, Houston, Tex.

[21] Appl. No.: 446,895

[22] Filed: Dec. 6, 1989

[30] Foreign Application Priority Data

Dec. 15, 1988 [GB] United Kingdom .................. 8829307

[51] Int. Cl.$^5$ ...................... G01N 33/24; E21B 49/08
[52] U.S. Cl. .................................. 364/499; 73/153; 436/25; 175/42; 166/250
[58] Field of Search ................ 364/499; 73/151, 153, 73/154; 175/42; 436/25, 27; 166/250

[56] References Cited

U.S. PATENT DOCUMENTS

| | | | |
|---|---|---|---|
| 2,772,951 | 12/1956 | Bond | 436/31 |
| 3,409,092 | 11/1968 | Doremus | 175/50 |
| 3,433,312 | 3/1969 | Burdyn et al. | 60/641.7 |
| 3,512,164 | 5/1970 | Bynum | 73/153 |
| 3,766,993 | 10/1973 | Fertl et al. | 175/50 |
| 3,766,994 | 10/1973 | Fertl | 175/50 |
| 3,802,259 | 4/1974 | Eckels | 73/153 |
| 3,899,926 | 8/1975 | Haden | 73/153 |
| 4,306,879 | 12/1981 | Allen et al. | |
| 4,369,655 | 1/1983 | Scearce | 73/153 |
| 4,385,666 | 5/1983 | Mamadzhanov et al. | 175/40 |
| 4,447,340 | 5/1984 | Fery | 175/42 |
| 4,472,354 | 9/1984 | Passell et al. | 436/38 X |
| 4,495,800 | 1/1985 | Wilcox | 73/61.4 |
| 4,507,210 | 3/1985 | Lauzon | 252/8.5 A |
| 4,546,252 | 10/1985 | Dion | 250/252.1 |
| 4,635,735 | 1/1987 | Crownover | 175/48 |
| 4,790,933 | 12/1988 | Quigley et al. | 73/153 X |
| 4,807,469 | 2/1989 | Hall | 436/27 |
| 4,833,915 | 5/1989 | Radd et al. | 73/153 |
| 4,878,382 | 11/1989 | Jones et al. | 73/153 |
| 4,887,464 | 12/1989 | Tannenbaum et al. | 73/153 |
| 4,904,603 | 2/1990 | Jones | 436/25 |

FOREIGN PATENT DOCUMENTS

| | | |
|---|---|---|
| 1222933 | 6/1987 | Canada . |
| 2498332 | 1/1980 | France . |
| 2066951 | 1/1981 | United Kingdom . |

OTHER PUBLICATIONS

"Continuous Determination Drilling Mud", by Brad Mills, *The Oil Weekly*, Aug. 1, 1938.
"Determination of Free Chromate in Lignosulfonate Dispersants By Ion Chromatography with Atomic Absorption Spectrometric Detection", by Jarl M. Pettersen, Analytica Chimica Acta, 160 (1984) pp. 263–266.

*Primary Examiner*—Joseph L. Dixon
*Attorney, Agent, or Firm*—Henri Dupont; Martin Hyden; John J. Ryberg

[57] ABSTRACT

In the rotary drilling of oil wells a drilling mud is used both to transport the cuttings up to the surface and to impose an hydrostatic pressure on the walls of the borehole. For these functions the mud must for example have an acceptable viscosity and density. It is therefore important to monitor the characteristics of the mud, and to keep them within certain limits. Only recently, however, has drilling practice recognized the importance of monitoring the mud's ionic composition. The various techniques proposed involve separation of the mud into liquid and solid portions, and analysis of these. Though they have proven useful, yet there are a number of problems. For example, the separation has not always been easy, and the available techniques often may not satisfactorily remove the fines. The invention suggests that these two problems, at least, can be overcome by the relatively simple expedient of first acidifying the mud sample, for acidification both causes the mud particles to flocculate, and so be more easily separated off, and causes the active fines to dissolve. In a preferred embodiment hydrobromic acid is employed, together with tetramethylammonium bromide (a displacement agent enabling the mud solid's Cationic Exchange Capacity to be measured), the separation is by filtration, and the analysis is by ion chromatography—and the results are fed into a computer model that then calculates the original mud components.

26 Claims, 2 Drawing Sheets

METHOD FOR THE DETERMINATION OF THE IONIC CONTENT OF DRILLING MUD

TECHNICAL FIELD

This invention relates to the monitoring of drilling mud, and concerns in particular a method for monitoring changes in the chemical composition of the mud, preferably by ion chromatography at the rig site during drilling operations.

BACKGROUND OF THE INVENTION

In the rotary drilling of wells, such as hydrocarbon (oil and gas) wells, a mud is continuously circulated from the surface down to the bottom of the hole being drilled and back to the surface again. The mud—usually a fluid mixture of a clay such as bentonite suspended in a continuous phase such as water—has several functions. One of these is to transport the cuttings drilled by the drill bit up to the surface where they are separated from the mud. For this purpose the mud must be viscous enough to entrain the cuttings yet fluid enough to pump. Another function is to impose an hydrostatic pressure on the walls of the borehole so as to avoid a collapse of the borehole and an influx of gas or liquid from the formations being drilled. For this function the mud must be dense enough to resist formation pressure, yet not so dense that its pressure forces it deep into the formations, possibly fracturing them. It is therefore important to monitor the characteristics of the mud, and to keep them within certain limits. Weighting materials, barite for example, are added to the mud to make it exert as much pressure as needed to contain the formation pressures. Clay is added to the mud so as to keep the drilled cuttings in suspension as they move up the hole. The clay also sheathes the wall of the hole (this thin layer of clay, called mud cake, forms a permeability barrier, and prevents or reduces fluid loss). Numerous chemicals are available to give the mud the exact properties it needs to make it as easy as possible to drill the hole, and the importance of the mud, and the difficulties of controlling its composition, can be further appreciated from the following additional comments.

Maintaining the stability of the borehole is one of the major problems encountered in drilling oil and gas wells. It has been observed in the field that holes in shale sections frequently go out of gauge, due to loss of material from the borehole wall. This material can become detached from the wall in the form of large fragments (cavings), which are normally carried to the surface by the circulating mud, just as the drilled cuttings are. However, if the hole-cleaning capacity of the mud is insufficient, cavings collect on ledges, and may cause the drill pipe to stick on pulling out of the hole. The necessity to re-drill through fill accumulated on the bottom of the hole during trips is another result of the process.

Moreover, regardless of the efficiency of the cavings removal, in all cases there is inevitably a gradual build-up of dispersed particles in the mud, which particles are too fine to be removed by the solids control equipment. This may give rise to a host of secondary problems. For instance, the increased solids content slows down the drilling rate, and, as drilled solids form a poor filter cake, problems in controlling the fluid loss may cause differential sticking on permeable sands. In addition, there may be difficulty controlling the mud weight, leading to lost circulation, and an unstable rheology.

In some circumstances, shales swell in contact with the mud in such a way that the well bore diameter decreases. In such cases, identified in the field by a need for frequent reaming, the well bore closes down on to the drill string, and there is once again an increased risk of pipe sticking.

The various forms of hole instability resulting from the interaction between the drilling fluid and the subterranean formations penetrated by the borehole are related to the hydration and dispersion of the clay sediments.

It is known that during the drilling process the ionic composition of the drilling mud changes from its original formulation. These changes in composition are in part a measure of downhole processes which may be termed mud-rock interactions. An important example of mud-rock interactions is ion exchange between cations in the mud and in shale formations. Until recently drilling practice has not required the ionic composition of the mud to be monitored, so that the extent of these interactions has not been determined, and the composition of the drilling mud has not been accurately maintained. However, in the Specification of our co-pending Application for European Patent No: 88/301,856.6, we have described how important such a monitoring process is, and how useful it can be. In general, in that Specification we described a method for controlling the drilling of boreholes by determining the ionic compositions of the drilling muds and/or drilled cuttings in order to monitor various chemical processes which occur in the well bores, e.g. salt water influxes, changes in the solubility of salts with changes in pH, and cation exchange processes involving the cations added to the water-base mud (e.g. potassium, calcium) to stabilise shale sections.

The various general and preferred methods of the earlier invention have proven useful in the control of drilling mud composition, and yet our further research has indicated that there may nevertheless be a number of problems. For example, the separation of the liquid part of the mud by filtration has not always been easy, for, dependant on the mud's type, its clay components often fulfil only too well their intended purpose (to sheathe the well bore wall with the thin, impermeable "mud cake" layer), and in just the same way form an almost impenetrable layer in the filter apparatus, so reducing the flow of liquid therethrough to almost nothing, even when filtering under several atmospheres pressure. Again, the filter techniques may not always satisfactorily remove the fines (the very small particles generated, for instance, by the drilling procedure), and if the fines in a mud sample dissolve on dilution of the sample, as will carbonate fines, then this can seriously affect the ionic concentrations, and so give rise to significantly misleading analytical results.

DETAILED DESCRIPTION OF THE INVENTION

We have now found that these two problems, at least, can be overcome by the relatively simple expedient of reducing the pH of the mud sample before its further treatment by filtration and analysis, for pH reduction brings two immediate improvements in the characteristics of the mud. Firstly, the manner in which the clay components of the mud are dispersed changes dramatically; the fine, almost colloidal, mud particles flocculate—that is, aggregate into large, coarse, clumps—so that the resulting "lumpy" dispersion becomes very much easier to filter. Secondly, the active fines—specifically, those carbonate fines that would normally pass through the filter in solid, undissolved form, to cause misleading analytical results—are dissolved, and the filtrate, upon dilution, provides correct ion chromatogaphic analyses.

In one aspect, therefore, this invention provides a method for the determinatin of the ionic components of a drilling mud, in which method:

a suitable sample of the mud has its pH reduced, to flocculate the clay components thereof, and to solubilize any undissolved active materials therein; and the resultant product is then separated into solid and liquid parts, and the liquid part is subjected to analysis to determine its ionic content.

The ionic components of a drilling mud may be ions of many types, in many forms. The principal ones of interest, however, are the potassium, sodium, calcium and magnesium cations, and the chloride, sulphate and bromide anions—and the carbonate and bicarbonate anions (it is these latter that can cause difficulties, for in the presence of calcium and/or magnesium cations they can form undissociated, insoluble, calcium and/or magnesium carbonate and bicarbonates). The matter is discussed further hereinafter in connection with the preferred method of analysis, ion chromatography.

The method of the invention appears to be applicable to the determination of any variety of water-based (as opposed to oil-based) drilling mud. A typical water-based mud—and hereinafter references to mud are to water-based mud, unless some other meaning is clearly intended—is one that is essentially a suspension of a bentonite clay in water (usually sea water, where the drilling takes place off shore) together with various additives for viscosity, pH and density control. For example, such a bentonite/sea water mud might contain the following components:

| Seawater-dispersed Mud | | |
|---|---|---|
| Component | Function | Amounts (Kg/m$^3$) |
| bentonite | primary viscosifier | 36 |
| XC-polymer | viscosifier | 1 |
| CMC low viscosity | fluid loss control | 10 |
| CMC high viscosity | viscosifier, fluid loss | 2 |
| chrome lignosulphate | dispersant | as req. |
| sodium hydroxide | pH control | 3 |
| sodium carbonate | calcium control | 0.9 |
| barite | mud density | as req. |

CMC is CarboxyMethyl Cellulose.
XC is a polysaccharide produced by the action of the plant pathogen Xanthomonas Campestris on carbohydrates.

Other common types of mud contain the following components:-

| Component | Function | Amounts (Kg/m$^3$) |
|---|---|---|
| Freshwater-dispersed Mud (Density = 1,500 Kg/m$^3$) | | |
| bentonite | primary viscosifier | 57 |
| chrome lignosulphate | dispersant | 9 |
| lignite | dispersant/thinner | 6 |
| sodium hydroxide | pH control | 3 |
| barite | weighting agent | 600 |
| Potassium/Polymer Inhibitive Mud (Density = 1,500 Kg/m$^3$) | | |
| bentonite | primary viscosifier | 45 |

-continued

| Component | Function | Amounts (Kg/m$^3$) |
|---|---|---|
| CMC low viscosity | fluid loss control | 1.5 |
| potassium hydroxide | potassium/pH control | 4.5 |
| XC-polymer | shale inhibition | 9 |
| calcium hydroxide | calcium control | 13 |
| barite | weighting agent | 600 |

The method of the invention starts, naturally, by taking a suitable sample of mud. In principle this mud sample can be taken from anywhere in the system, but in general it is convenient to sample the return mud twice—once after it has just emerged from the lore (and the cuttings separated off) and again just before it is re-circulated back down into the well bore (after any additive treatment). The first of these provides information about what is happening to the mud down hole, whilst the second provides a check that the subsequent treatment did indeed restore the mud to its optimum composition. In practice, the first sample is conveniently taken immediately below the shale-shaker, and the second is taken either downstream from the active tank or in the flow line to the drill pipe. The matter will be most clearly understood from a consideration of the accompanying Drawings, in which:

BRIEF DESCRIPTION OF THE DRAWINGS

FIG. 1 shows the mud circulation equipment. The mud 10 is contained in a mud pit 12, called the active tank. A pump 14 draws up the mud from the pit through a pipe 16, and forces the mud through the discharge line 18, the stand pipe 20, the rotary hose 22 and the swivel 24. The mud then flows into the kelly 26 and down the borehole 28 in the drill pipe 30 and the drill collars 32. The mud reaches the bottom of the hole at the drill bit 34, and then flows up to the surface in the annulus 36 and in the mud return line 38. The mud then falls over a vibrating screen-like device 40, called a shale shaker.

Figure 1:
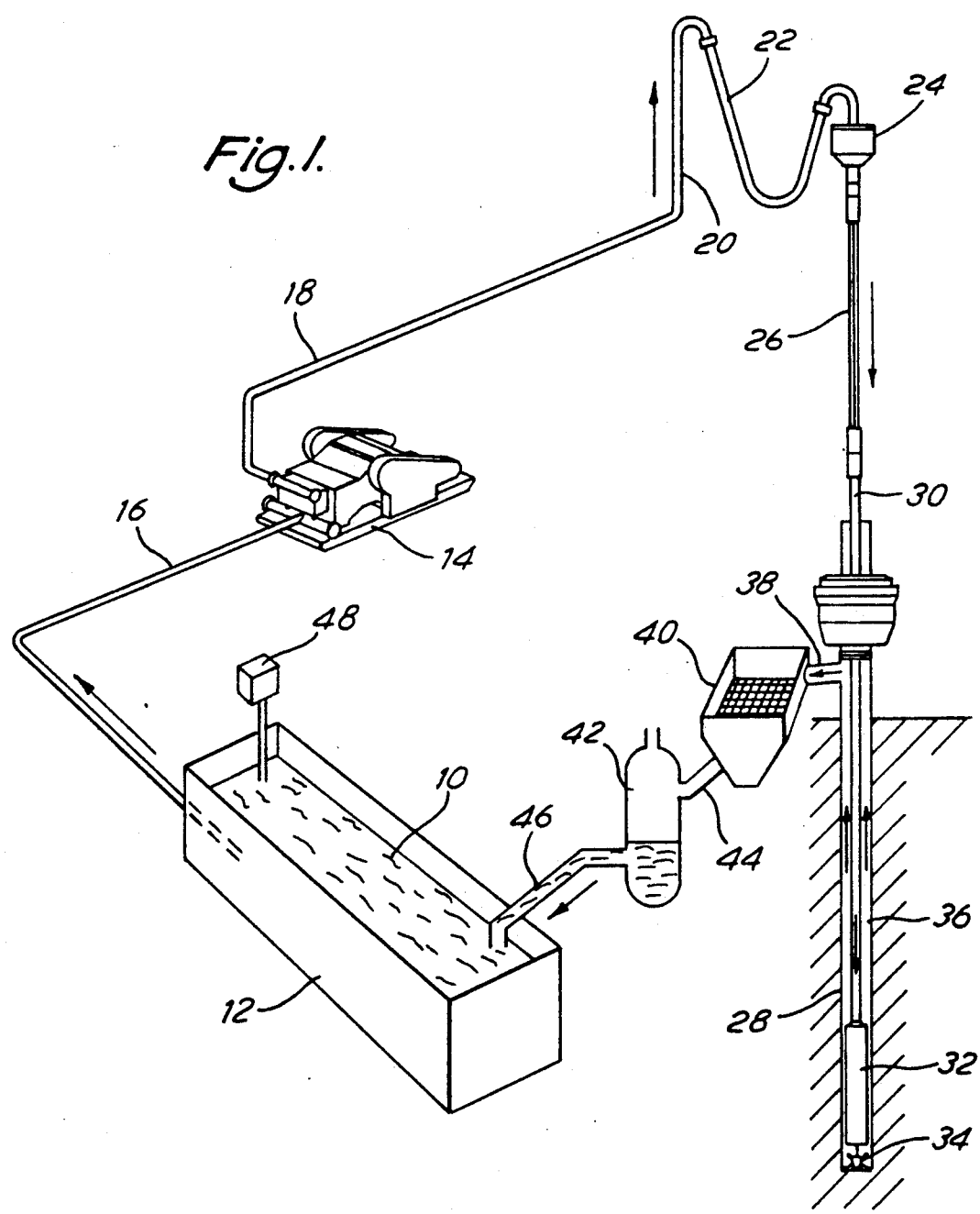
FIG. 1 is a schematic representation of a mud circulation equipment.

The role of the shale shaker is to separate from the liquid phase of the mud the cuttings drilled by the bit 34 and transported up in the annulus by the mud. The separation is made by having the mud pass through a screen which vibrates. The solids (called the cuttings) which are larger than the mesh size of the screen don't pass through the screen, and are rejected either in a reserve pit (when the drilling rig is on land) or in a barge or the sea (when the drilling operations are conducted offshore). The solid particles contained in the mud which have a size smaller than the mesh size of the screen pass through the screen, and therefore remain in the mud. These fine solids comprise part of the weighting material added to the mud to reach a certain mud density, as well as fine solids from the formations traversed by the borehole.

After the shale shaker 40, the mud flows into the solids control equipment, represented schematically by 42, through the pipe 44. The solids control equipment 42 could include a degasser, a desilter and a desander (these are not shown separately here). Then the mud falls into the pit 10 through the pipe 46. A mud-mixing hopper 48 is generally used to add solid materials like clay and barite to the mud in the active tank.

In the practice of the invention mud samples should be taken from both the active tank 12 or preferably downstream from a sampling tap on line 16 and from the pipe 44 between the shale shaker 40 and the solids control equipment 42. The sampling should be effected at known times, and at frequencies relevant to the application concerned (for example, for general mud engineering, every eight hours or so may suffice, whereas for lithological determination more frequent samples—say, every 15 minutes—may be required).

In the method of the invention, then, preferably two samples are taken, one of the mud as it is on exiting the well bore, and before any treatment, and the other as it is just prior to being pumped into the well bore, and after any treatment. From a purely mechanical point of view, each mud sample is conveniently placed in a small sample bottle such that the mud completely fills the bottle (care is taken to ensure that no air space is present in the sample bottle, thus minimising any reduction in pH caused by the absorption of carbon dioxide from the air).

Having obtained the mud sample, the first proper stage in the method of the invention is to reduce the pH of the sample, so as to cause the clay components to flocculate, and the undissolved active solid solid materials to dissolve.

In principle, this reduction can be effected simply by adding an acid, but in practice this may result in a serious problem, for as the pH drops to below 7—to around 4 or 5, say—the conversion of the carbonates in the sample proceeds through the desired bicarbonates and then to carbonic acid, which immediately dissociates into water and gaseous carbon dioxide, and the latter bubbles off, and is lost to the system (unless special precautions are taken). Consequently, the subsequent analytical stage records a carbonate content less than the true carbonate content of the mud sample before pH reduction—such a result would be misleading.

Accordingly, the pH reduction is most conveniently carried out in one of two preferred ways. Firstly, it can be effected using an acid, so long as it is done in a "closed" system, from which the released carbon dioxide cannot escape. Once the acid has done its work, dissolving the fines, the pH is then raised (to around 7—neutrality), and the still-dissolved carbon dioxide gas is converted back to bicarbonate, to give a correct analysis.

Alternatively, the pH reduction can be carried out using a buffer solution that will maintain the pH at a level—around 8 to 9—where the carbonate conversion proceeds only to the intermediate bicarbonate, and not through to carbonic acid (and gaseous carbon dioxide). Unfortunately, using a "neutral" buffer in this way is rather slow—the reaction kinetics for dissolution of solid carbonates are very much slower than using an acid proper, at a pH around 4 to 5—but for some purposes this may be acceptable.

Where an acid is employed it may be almost any acid, mineral or organic. Mineral acids are generally preferred, for not only are they cheaper but it may be desired to analyse the mud for organic materials in addition to the usual inorganic ions, so that preferably no more of these are added in the acidification. However, because use of the more common mineral acids—sulphuric and hydrochloric—will obscure the quantities of the two principal inorganic anions being determined (sulphate and chloride) it is best to employ an acid with a somewhat less confusing anion. Thus, hydrobromic acid is the preferred acid.

Where a buffer solution is used much the same considerations of cost, convenience and results-obscuration still apply. A propitious buffer is a conventional borate/boric acid buffer (with a pH of about 7.6); another possibility is tri(hydroxymethyl)aminomethane (TRIS), together with some boric acid (which has a pH of about 8.2).

The amount of acid or buffer employed is sufficient to cause both flocculation and solubilisation—and how much that is depends to some extent upon the original pH of the mud (and how much undissolved fines it carries). In general, however, muds will have pHs in the range 9 to 12, and the desired degree of flocculation, and the certainty of fines dissolution, can be achieved by reducing that to 6 to 8 (around neutrality) or slightly below. Of course, if the pH is reduced to a level at which there is a significant likelihood of any bicarbonates formed releasing their $CO_2$ (the loss of which from the sample would possibly result in an inaccurate analysis), then the reduction should be done in a closed system.

The pH reduction causes dissolution of any undissolved active—that is, basic—fines in the mud. These active fines will for the most part be carbonates, specifically calcium and magnesium carbonates, present as minute solid particles in a complex equilibrium with dissolved calcium and magnesium bicarbonate, and dissolved carbon dioxide ($CO_2$). pH reduction shifts the equilibrium such that all the carbonate salts dissolve to give what is in effect dissociated calcium/magnesium bicarbonate.

Although the pH reduction will normally cause sufficient flocculation to give an acceptable improvement in filterability, further improvement can, if desired, be achieved by adding one or more of the many materials specifically known for their flocculating ability. A typical example of a class of these materials is that of the polymeric anions—for instance, partially hydrolysed polyacrylamides such as those available from Allied Colloid under the names MAGNAFLOC and ZETAG (these are commonly used for the removal of undesirable solids from drinking water, or for the preparation of solids-laden water for discharge into the environment). Another useful class of flocculating agents is quaternary ammonium compounds, such as tetrabutylammonium bromide. All these flocculants tend to be extremely efficient, and can be used in very low concentrations—thus, around $10^{-3}$ molar.

Having reduced the mud's pH, causing flocculation of the clays and dissolution of the fines, the resultant material is separated into its solid and liquid components (with the various ions to be determined being in the latter). The separation may be effected by any of the usual ways—thus, by centrifuging, for example, to give a supernatant liquor and a solid residue—but pressure filtration is generally more convenient (and, because of the initial flocculation, relatively easy). Hereinafter it is, for convenience in referring to the liquid portion, assumed that it is indeed a filtrate.

The separated liquid portion of the mud is then subjected to analysis to determine the ionic constituents thereof, both as regards their kind and as regards their quantity.

There are various ways this analysis could be performed, including a classical chemical analysis, but most conveniently it is carried out by the technique of ion chromatography. A major advantage of this technique is its ability to identify anion species, in contrast to most other techniques—e.g., atomic absorption spectroscopy, flame emission photometry, or inductively coupled plasma [ICP]). Further advantages of an ion chromatography system are its sensitivity (resolution down to about 1 part per billion), precision (better than 0.5% based on peak area), and ability to differentiate ionic species with generally small interference effects. The principles of operation and general use of ion chromatography are well known.

In the present invention, a mud filtrate ion may be a "principal" ion and of interest for one or more of a number of reasons. It may have a significant effect on mud properties at any concentration, which is frequently the case when it is a deliberate special additive to the mud; it might be one giving rise to potential environmental problems if discharged even at low concentrations. All mud filtrate ions of interest could be assessed by ion chromatography, but are not necessarily so assessed. Thus, hydrogen and hydroxyl ion concentrations can be provided by pH measurement, and carbonate and bicarbonate ion concentrations can be deduced from the measured concentrations of other ions. Of the principal mud filtrate ions present which are suitable for ion chromatography, not all need to be measured, though at least one cation concentration and at least one anion concentration are measured in this way. Typical principal mud filtrate ions for determination by ion chromatography are sodium, potassium, calcium, magnesium, chloride, sulphate and carbonate.

At the locations where the samples are taken, the pH and temperature of the mud are measured and logged by combined probe inserted into the mud stream. Each mud sample is then transferred to a separator, and the filtrate is injected into the three ion chromatography units simultaneously to determine its anion, monovalent cation and divalent cation contents. It may be necessary to dilute the filtrate by some suitable factor to ensure that the analyte concentration is in the optimum range of the ion chromatography system. Thus, while freshwater-based filtrates will rarely require dilution, seawater-based filtrates may need diluting by a factor of 100. The pH of the filtrate (undiluted) is determined at ambient temperature, and corrected to the value at the temperature recorded at its sample point.

Once the analysis has been completed, the results can be used to calculate the quantities of ionic constituents in the mud. The various stages involved are described in detail in the Specification of our aforementioned European Application; a version thereof is used in the Examples given hereinafter.

In the invention of our aforementioned European Application it is suggested that the mud solids may be analysed instead of or in addition to the mud filtrate, and it is pointed out that the current practice in the oilfield on the analysis of the solid component of the mud is the determination of its cation exchange capacity (CEC) using the methylene blue test. The main object of this test is to determine the build-up of dispersed clay minerals from drilled shale whose particle size is too small for removal by the drilling rig's solids control equipment. It is then stated that in accordance with that invention, an ion chromatography system is used to provide an accurate measure of the CEC of the mud solids, and to identify the exchange cations of the clay minerals during the drilling process, and it proposes using tetramethylammonium bromide to displace the exchange cations in the mud solids. In the present invention this may be effected, as well—but instead of carrying out this displacement upon a separated sample of the mud solids it is very much preferred to effect it upon the whole mud prior its separation into liquid and solid portions. Thus, the present invention most preferably includes a stage in which an excess of a displacement agent is added to the mud sample prior to its separation, whereby the cations carried by the mud solids as a result of their cation exchange capacity are displaced into solution, thereafter to be separated off with the liquid portion. By determining how much of the displacement agent remains free in the liquid, and from a knowledge of how much was added, there may be calculated the quantity of displaced cations—and thus the cation exchange capacity (CEC) of the mud solids.

The displacement agent to be used is an ion exchanger that is highly selected by the clay in preference to the ions initially absorbed thereon. However, the exchanger should not be too highly selected, else it will also be strongly absorbed onto the active sites in the ion chromatograph's ion exchange column, and will be difficult (and slow) to elute out as the sample proceeds down the column during the analytical stage. Typical exchangers selected by clays are the quaternary ammonium salts (many of which are also excellent flocculating agents), and the lower alkyl salts, such as tetramethylammonium bromide, are particularly satisfactory for use as displacement agents.

The addition of the displacement agent may be effected at any time, but—in order to avoid hydrolysis of the clay content of the mud confusing the results—preferably not significantly after the mud sample is acidified. The exchange cations associated with the mud solids are of course an integral part of the cations in the mud system. The contribution $C_i^{ms}$ of exchange cation i in the mud solids to the total content of i in the mud is given by $$C_i^{ms} = \bar{x}_i CEC(1-w_a)d_m$$

where $\bar{x}_i$ is the fraction of the cation exchange capacity (CEC) of the mud solids occupied by cation i, $w_a$ is the weight fraction of the water in the mud, and $d_m$ is the mud density.

The method of the invention provides a determination of the ionic components of a drilling mud. Though the determined ion values may be useful as they stand, it is preferred to employ these values as a basis for a calculation of the molecular components—that is, the compounds, both dissociated and undissociated, and in both dissolved and undissolved form—that were in the original mud sample at the conditions of temperature, pressure, pH and so on that were extant when it was taken. Reactive combination of the primary ionic components leads to a distribution thereof through a range of chemical species which includes free hydrated ions, aqueous complexes, ions bound to clay surfaces, and elements bound into solid mineral phases. Predicting the concentrations of these species from the analyses requires a method of calculation based on mass balance, whereby the total concentration of each primary component is equated to the sum of the concentrations of that component bound into each chemical species in existence. A second set of constraints is given by the well-established laws of classical thermodynamics, which govern the relationships between the concentrations of chemical species present at equilibrium. The essential features of such predictions involve establishing the equilibrium constants for all reactions known to occur between the primary components, constructing the mass balance equations, and solving numerically for each species concentration. This yields output data containing the concentrations of all aqueous ionic species, of any minerals present, and of any ions bound to clay edges and surfaces, and the pH. Details of the chemical and numeric techniques are given in F Morel's & J Morgan's "A numerical method for computing equilibria in aqueous chemical systems", 1972, Env. Sci. and Technology, 6, 58. This type of calculation can be done by hand, iterating the computations until any changes from one iteration to the next are insignificant. However, such a task is especially suited to a computer, and there are in fact available a number of computer models that will produce a reasonably accurate assessment of the original mud ionic components based upon the ion analysis figures obtained from the sample, some of which models are designed to be extended by the inclusion of additional thermodynamic data in a complementary database. One such recommended for this purpose is GEOCHEM (see G Sposito's & S V Mattigod's "GEOCHEM: A computer Program for the calculation of Chemical Equilibria in Soil solutions and other Natural Water Systems", 1980, Kerney Foundation of Soil Science, University of California, Riverside). The model comes fully equipped with all the thermodynamic data. Other models are:

| | |
|---|---|
| MINEQL | J. C. Westall, J. L. Zachary, & F. M. M. Morel, "MINEQL: A computer program for the calculation of chemical equilibrium composition of electrolyte solutions", 1976, Tech, Note 18, Ralph M. Parsons Lab., MIT, Cambridge |
| EQ3NR | T. J. Wolery, "EQ3NR: A computer program for geochemical aqueous speciation-solubility calculations", 1983, User's Guide and Documentation, UCRL-53414, Lawrence Livermore National Laboratory, Livermore, California, USA |

(both these require their databases equipping with equilibrium constants for ion exchange reactions, and some modifications to the numerical techniques they employ).

The numerical techniques used in all these models are roughly similar, and will yield similar predictions of speciation. The differences for the most part due simply to the use of slightly different activity coefficient expressions and thermodynamic data. A useful range of data can be obtained from L V Benson & L S Teague, 1980, Lawrence Berkeley Lab., Univ. California, LBL-11448.

As explained in detail in our aforementioned European Application, the assessment of the original mud components based upon the determined ion values is most conveniently made part of a larger system that outputs recommendations as to how the actual, present, mud components should be modified to attain the optimum values for the conditions currently being encountered down hole. More specifically, the measurement of the ionic composition of the mud filtrate is accompanied by a rig-site, computer-based interpretation giving continuous information on the chemical composition of the mud and the extent of the mud/formation interactions; this is associated with an advisory module recommending appropriate changes in the mud formulation.

EXAMPLES

The following Examples are now given, though by way of illustration only, to show details of various embodiments of the invention.

Description of General Procedure and Calculations for Whole Mud Analysis

The mud samples used for whole mud analysis are taken from the circulating mud system of a drilling rig. Two sample types in particular are identified: samples of mud from the active tank (or the flow line between the active tank and the drill pipe), and return mud samples taken from immediately below the shale shaker but before the solids control equipment.

An accurately known volume of mud $V_m$ is weighed ($M_m$) to determine the density $p_m$ of the mud. A sample of the mud is dried to determine the uncorrected weight fraction solids content $W'$ defined by $$W' = \frac{M_m - M_w}{M_m} \tag{1}$$

where $M_w$ is the weight of water lost on drying the mud to constant weight at a minimum temperature of 105° C., but preferably closer to 160° C. The weight of remaining solid is composed of the true mud solids $M_s$ and the weight $M_e$ of salts from the evaporated filtrate. The weight of solute $M_e$ in the filtrate will be determined by chemical analysis.

The volume fraction $v_w$ of water in the mud is given by $$v_w = \frac{V_w}{V_m} = \frac{M_w}{p_w V_m} \tag{2}$$

and the volume fraction $v_s$ of mud solids is thus $(1 - v_w)$. The average density $p_s$ of the mud solids is $$p_s = \frac{M_s}{V_s} = \frac{M_m - M_w - M_e}{V_m - V_w} \tag{3}$$

where the volume of filtrate $V_w$ associated with the mud is $M_w/p_w$. The density of pure water can be used in the above calculations if the ionic strength of the filtrate is sufficiently low. When mud filtrates have a high ionic strength, e.g., salt-saturated muds, the density (i.e., partial molar volume) of water can be calculated.

Acidification and Displacement

An accurately known weight of mud is removed from the bulk mud, and the pH measured; the pH of the mud is assumed to be equal to that of the solids-free filtrate. As explained hereinbefore, several methods in accordance with the invention can be used to dissolve the insoluble salts (such as calcium carbonate) and place the exchange cations from the clay solids into solution.

Closed System

If the mud is analysed as a closed system—i.e., not in equilibrium with the carbon dioxide in the atmosphere—then the pH of the mud can be lowered to about pH=5 by acidification without loss of carbon dioxide. Complete carbonate dissolution is achieved at this pH, and the carbon dioxide remains in solution. The cations on the clay solids can be placed into solution by exchange with a highly selected cation such as tetramethylammonium, which is added to the mud as the bromide salt. The acidification and ion exchange reaction for a closed system can therefore be achieved by treatment of the whole mud with a mixture of a mineral acid, such as hydrobromic acid, and tetramethylammonium bromide; typical concentration are $3 \times 10^{-3}$ and $5 \times 10^{-3}$ Molar, respectively.

The accurately-known volume $V_r$ of $(Me)_4NBr/HBr$ added to the mud depends on the estimated ionic strength of the mud filtrate and solids content. A dilution factor D is defined by $$D = \frac{V_w + V_r}{V_w} \quad (4)$$

and it is recommended that D should be chosen to be at least 10—and very preferably in the range 100 to 500.

Open System

If the mud is to be analysed as an open system, where the acidification would result in the loss of carbon dioxide to the atmosphere, then an alternative technique must be applied. The insoluble salts are dissolved in a buffer fixed at about pH=8, which ensures that the carbonate is converted to bicarbonate and remains in solution. The preferred buffer is the two-part system boric acid plus tris(hydroxymethyl)aminomethane (this latter component is referred to generally as "TRIS"), which, together with mannitol (hexahydroxy-hexane), constitutes a preferred eluent for use in the chemically-unsuppressed ion chromatography technique. Thus, the insoluble salts in the mud are dissolved into an excess of the unsuppressed anion eluent; the typical composition of the eluent is $6 \times 10^{-3}$ molar TRIS, $25 \times 10^{-3}$ molar mannitol, and $8.5 \times 10^{-3}$ molar boric acid, giving a buffer at pH=8.2.

The release of the exchange cations from the clay solids into solution is effected by the addition of tetramethylammonium bromide. Typically, dilution factors of about 500 are required for this technique.

Separation

The solid and liquid phases in the treated mud are separated by either centrifugation or by a high pressure filtration device, e.g., the API (American Petroleum Institute) filter press. The solid-liquid separation is easier to perform in the treated mud since the volume fraction of solids is lower and the addition of acid/buffer has lowered the pH which causes the clay solids to flocculate. Further, the problem of the presence of carbonate and hydroxide fines in the filtrate after separation, particularly by centrifugation methods, is removed.

Analysis

The treated mud filtrate is analysed for monovalent and divalent cations and anions using three separate ion chromatography units. All of the anions and cations of interest except carbonate can be determined by the chemically suppressed techniques of ion chromatography. The measurement of carbonate concentration is determined by the chemically unsuppressed method of ion chromatography.

The cation exchange capacity of the mud solids is determined by comparing the concentration of $(Me)_4N^+$ before and after addition to the mud. A convenient way to measure this difference is to subtract the chromatography of $(Me)_4N^+$ in the treated mud filtrate from that of the initial $(Me)_4NBr/acid$ (or/buffer) mixture. The difference chromatograph is accurately calibrated to give the uptake of $(Me)_4N^+$ by the clay solids; the exchange cations are unknown at this point.

The ion chromatography analysis gives the total composition of available ions in the mud system. For example, the total available calcium content of the mud consists of the calcium concentration of the filtrate (i.e., the calcium in solution), the calcium in the insoluble salts (e.g., calcium carbonate), and the exchange calcium ions on the clay surfaces. In general these three components will be in equilibrium with each other in the mud system, and any change in the concentration of one component may lead to changes in the concentration of the other two. The distribution of ions between the three components can be altered by chemical additions to the mud, either in the form of mud products at the surface or materials from the borehole.

Mud Component Assessment

The chemical composition of the treated filtrate can therefore be thought of as consisting of three parts: the diluted mud filtrate, the dissolved salts from the mud solids, and the exchange cations released by the excess of $(Me)_4N^+$ cations. A computer model is preferably now used to partition the total ionic composition into the filtrate, precipitated solids and exchange cations. Firstly, the CEC is calculated from the removal of $(Me)_4N^+$ ions, and the value is reported as both moles of monovalent exchange sites per kilogram of dry mud solids (or milliequivalents per gram of dry solid) and moles of exchange sites per liter of treated filtrate.

The ion concentrations determined by the ion chromatography systems, with the exception of the added tetramethylammonium and bromide ions, are multiplied by the dilution factor D to give their effective values i the original filtrate volume $V_w$. The CEC of the mud solids, measured as moles per liter of treated filtrate, is also multiplied by D to give the concentration of exchange sites in the original filtrate volume. These corrected concentrations are used in the computer model to give the equilibrium partition of the ions between filtrate, exchanger phase and precipitated solids. The model is run with the pH fixed to the value determined on the mud sample before treatment and with the mud closed to the atmosphere, i.e., the mud is not in equilibrium with the carbon dioxide in the atmosphere. The output from the model is the concentration of ions in the filtrate (together with the concentration of complex species, e.g., the ion pair $NaSO_4^-$), the nature of the exchange cations, and quantity of solid precipitated. The precipitated solids are a part of the mud solids, and are only brought into solution by the lowering of the pH.

The mud filtrate analysis allows the corrected solids content W to be determined from W' using $$W = W' - \frac{M_e}{M_m} = W' - \frac{TDS \times M_w}{\rho_w} \quad (5)$$

where TDS, the total dissolved solids in the filtrate, is $$TDS = \sum_i c_i M_i^m \quad (6)$$

where $c_i$ is the concentration of ion i and $M_i^m$ its molar mass.

Mud Solids Assessment

The whole mud analysis described above yields a number of measurements which can be used to quantify the reactive components of the mud solids.

The CEC of the mud solids, expressed as moles of monovalent exchange sites per kilogram of dry mud solids, is a measure of the clay content of the mud. For a given a reference mud formulation, the CEC and the solids content W (largely consisting of bentonite together with a weighting agent such as barite) are known. The measurement of W and the CEC will enable the build up of drilled clay solids to be diagnosed more accurately, and the actual efficiency of any treatment process used in an attempt to return the mud to specification can be measured.

An estimate of the weight fraction clay content $W_c$ (kg bentonite per kg of mud) of the mud solids which contributes to the solids content W can be estimated from $$W_c = \frac{(CEC)_{mud} \times W}{(CEC)_{bentonite}} \quad (7)$$

assuming that the CEC of the mud is due only to the presence of montmorillonite.

The insoluble carbonate/hydroxide content of the mud solids can be determined from the model computations which give the amount of solid precipitated per unit of original filtrate volume $V_w$. The contribution $W_p$ of these precipitated salts to the solids content W is given by $$W_p = \frac{V_w \times W}{M_m} \sum_i M_i^p \quad (8)$$

where $M_i^p$ is the weight of salt i per unit volume of filtrate precipitated by the model.

The remaining fraction of solids $W_r$, defined by $$W_r = W - W_c - W_p \quad (9)$$

therefore represents the chemically unreactive solids in the mud. These remaining solids are most likely to be barite, added as a mud product, and silica fines produced by drilled sandstone formations. The value of $W_r$ can be compared to the weight fraction of barite $W_b$ in the reference mud formulation to give an approximate barite content.

The change $\Delta W$ in the solids content of the mud can be compared with the measured value of $\Delta W_c$ (estimated from Eqn. 7 with $(CEC)_{mud}$ replaced by $\Delta (CEC)_{mud}$) and $\Delta W_p$ to determine the origin of the solids. In dispersing shale sections $\Delta W$ is expected to be largely accounted for by $\Delta W_c$, which is measured by the increase in the CEC of the mud solids. The CEC of the additional clay solids in the mud system can be determined by $$CEC = \Delta CEC \times (\Delta W - \Delta W_p) \times M_m \quad (10)$$

where the measurments of both the CEC and $\Delta W$ are made on the same mass of mud $M_m$. The estimation of the CEC of the added clay solids to the mud assumes that $\Delta W_r$ is zero.

The shale dispersion which has been discussed to date has been largely concerned with the dispersion of shales which are being drilled. The direct measurment of clay solids in the mud by CEC enables the dispersion of an open shale above the drilling process to be identified when non-shale formations are being drilled. For example, the clay solids produced by the dispersion of an open shale can be discriminated from the carbonate fines produced during the drilling of a limestone section.

In limestone or dolomite sections the mud solids will aquire $CaCO_3$ or $MgCa(CO_3)_2$ fines which are measured by an increase in $\Delta W_p$. The discrimination of $CaCO_3$ from $MgCa(CO_3)_2$ by chemical analysis will therefore allow limestone and dolomite sections to be identified without recourse to the usual practice of calcimetry.

EXAMPLE 1: WHOLE MUD ANALYSIS—BUFFER TREATMENT

Preliminary Preparation of a "Synthetic" Mud Sample

A representative example of a weighted bentonite and freshwater mud was made up from the following components:

| | |
|---|---|
| De-ionised water | 1000 g |
| Sodium sulphate | 0.178 g ($1.25 \times 10^{-3}$ M) |
| Sodium chloride | 0.292 g ($5 \times 10^{-3}$ M) |
| Calcite (calcium carbonate) | 10 g (0.1 M) |
| Bentonite (Montmorillonite) | 77 g |
| Barite (barium sulphate) | 391 g |
| Dispersant (lignosulphate) | 1.45 g |

The sodium sulphate and chloride are added to the water to simulate the effect of ions which originate from the boreholes (the source of the "fresh" water), and these concentrations will serve to check the validity of the analysis of the various mud treatments. Calcite is added to simulate the contamination of the mud by drilled limestone formations, and the precipitation of calcium carbonate caused by the addition of sodium bicarbonate (to reduce the calcium concentration in the filtrate).

First, the sodium sulphate and chloride, and the calcite, are dissolved/mixed with the water. The bentonite clay and the dispersant are then added, and the resultant suspension is sheared for several hours to achieve complete hydration of the clay. The pH of the mud is then adjusted to about pH 10 by the addition of sodium hydroxide. The barite is then added to increase the mud's density to the required value, and the whole is throughly homogenised, to give the desired synthetic freshwater mud. The mud density is 1.31 g/ml, and the solids content is 31.6 wt %.

The total ionic composition of the mud, including the ions in the filtrate, the calcite, and the exchange cations on the clay, is:

| Ion | Molar Concentration |
|---|---|
| $Na^+$ | $17.7 \times 10^{-3}$ |
| $Ca^{++}$ | 0.1 |
| $Cl^-$ | $5.4 \times 10^{-3}$ |
| $SO_4^{--}$ | $3.9 \times 10^{-3}$ |
| $CO_3^{--}$ | 0.102 |
| CEC Bentonite | $0.8 \times 10^{-3}$ moles/g dry clay |
| Exchange sodium conc. | 0.062 |
| Total sodium conc. | 0.080 |

It will be apparent that the sodium, carbonate and sulphate concentrations are larger than the added concentrations. This is due to the presence of impurities in the bentonite (analysis of an aqueous suspension of 77 g bentonite showed it to contain the following ion molar concentrations: $Na^+ = 1.02 \times 10^{-2}$; $Ca^{++} = 1.2 \times 10^{-4}$; $Cl^- = 3.5 \times 10^{-4}$; $SO_4^{--} = 2.6 \times 10^{-3}$; $CO_3^{--} = 2.6 \times 10^{-3}$). The figures in the Table above are part calculated (from a knowledge of what was used to make the mud) and part measured (to determine the impurities in the bentonite).

Whole Mud Analysis

1) Comparative Filtration of Untreated Mud

A sample of the mud, undiluted, was then filtered using an API (American Petroleum Institute) filter press. Pressure was applied with nitrogen at 100 psi (6.8 bar). The variation of the filtrate volume collected with time is shown by Line 1 in the graph of FIG. 2 of the accompanying Drawings. It will be seen that despite the high pressure less than 5 ml were collected in the first 5 minutes, and that within even as long as 30 minutes less than 10 ml had filtered through.

Two more samples of this mud were diluted 10 and 50 times respectively with water, and then filtered in the same way. The results are shown by Lines 2 and 4 of the graph of FIG. 2. It will be apparent that dilution makes a considerable, and apparently beneficial, difference; with the 10 times dilution, over 15 and nearly 40 ml were collected after 5 and 10 minutes respectively, while with the 50 times dilution nearly 50 ml were collected within 10 minutes.

However, analysis of the filtrates by ion chromatography showed anomalous results, thus:

| Ion | Molar Concentration ($\times 10^{-3}$) | | | |
|---|---|---|---|---|
| | actual | 0 times | 10 times | 50 times |
| $Na^+$ | 17.7 | 23. | 34. | 46. |
| $Ca^{++}$ | 100. | 1.2 | 1.6 | 4.6 |
| $Cl^-$ | 5.4 | 5.4 | 4.8 | 4.9 |
| $SO_4^{--}$ | 3.9 | 5.8 | 5.7 | 5.4 |
| $CO_3^{--}$ | 102. | 2.6 | 12. | 22. |

The chloride and sulphate figures are consistent with normal experimental error at these dilutions.

From the 10- and 50-times figures it is clear that the sodium and carbonate concentrations have apparently increased. This increase is probably due to two processes which are acting simultaneously during dilution; dissolution of the simulated calcium carbonate fines in the mud, and ion exchange between the calcium released into the filtrate and the sodium ions on the bentonite. For example, in the 10-times dilution data the carbonate concentration has increased by $9 \times 10^{-3}$ molar from the untreated mud filtrate while the calcium concentration has increased by only $0.4 \times 10^{-3}$ molar. The apparent charge imbalance between the calcium and carbonate concentrations ($8.6 \times 10^{-3}$ molar) is accounted for, in part, by an increase in the sodium concentration of $11 \times 10^{-3}$ molar. However, in neither the 10-times nor the 50-times dilution has all the known carbonate concentration been recovered; the dissolution has therefore only been partial. The other ion concentrations have remained largely the same. Thus, although dilution of the mud increases the rate of filtration, it can lead to misleading analytical results.

2) Preparation (pH reduction) of the Mud

A 10 ml sample of the synthetic mud described above was placed in a suitable container, and about 90 ml of TRIS buffer ($6 \times 10^{-3}$ M TRIS, $25 \times 10^{-3}$ M mannitol and $8.5 \times 10^{-3}$ M boric acid) were added thereto. The whole was thoroughly mixed, producing a 10-times diluted dispersion of the mud (and of its solids); its pH was thus reduced to, and fixed at, 8.2.

Filtration

A sample of the diluted, buffered mud was then filtered using an API filter press. The variation of the filtrate volume collected with time is shown by Line 3 in the graph of FIG. 2 of the accompanying Drawings. It will be seen that over 15 ml were collected in as little as 5 minutes, and that within 30 minutes nearly 50 ml had filtered through.

The filtrate was then subjected to ion chromatography. The results were as follows (with the pure water dilution figures in brackets):

| Ion | Molar Concentration ($\times 10^{-3}$) | | | |
|---|---|---|---|---|
| | actual | 10 times | 50 times | 500 times |
| $Na^+$ | 17.7 [23] | 40.1 [34] | NM. [46] | 75. [NM] |
| $Ca^{++}$ | 100. [1.2] | 3.2 [1.6] | NM. [4.6] | 101. [NM] |
| $Cl^-$ | 5.4 [5.4] | 4.7 [4.8] | NM. [4.9] | 23. [NM] |
| $SO_4^{--}$ | 3.9 [5.8] | 5.5 [5.7] | NM. [5.4] | 8. [NM] |
| $CO_3^{--}$ | 102. [2.6] | 14.1 [12.] | NM. [22.] | 101. [NM] |

(NM means "not measured")

It is not clear why these results appear to show a considerable increase in sodium and chloride, and a significant increase in sulphate.

The dilution of the mud with the buffer by a factor of 10, or even a factor of 50, may not cause dissolution of all the "solid" carbonate material therein. Accordingly, to ensure full dissolution it is desirable to dilute with buffer by a factor of 500.

EXAMPLE 2: WHOLE MUD ANALYSIS—ACID TREATMENT

Various samples of the synthetic mud prepared in Example 1 above were acidified with $10^{-3}$ molar hydrobromic acid. One sample was acidified/diluted by a factor of 10, another by a factor of 50.

Figure 2:
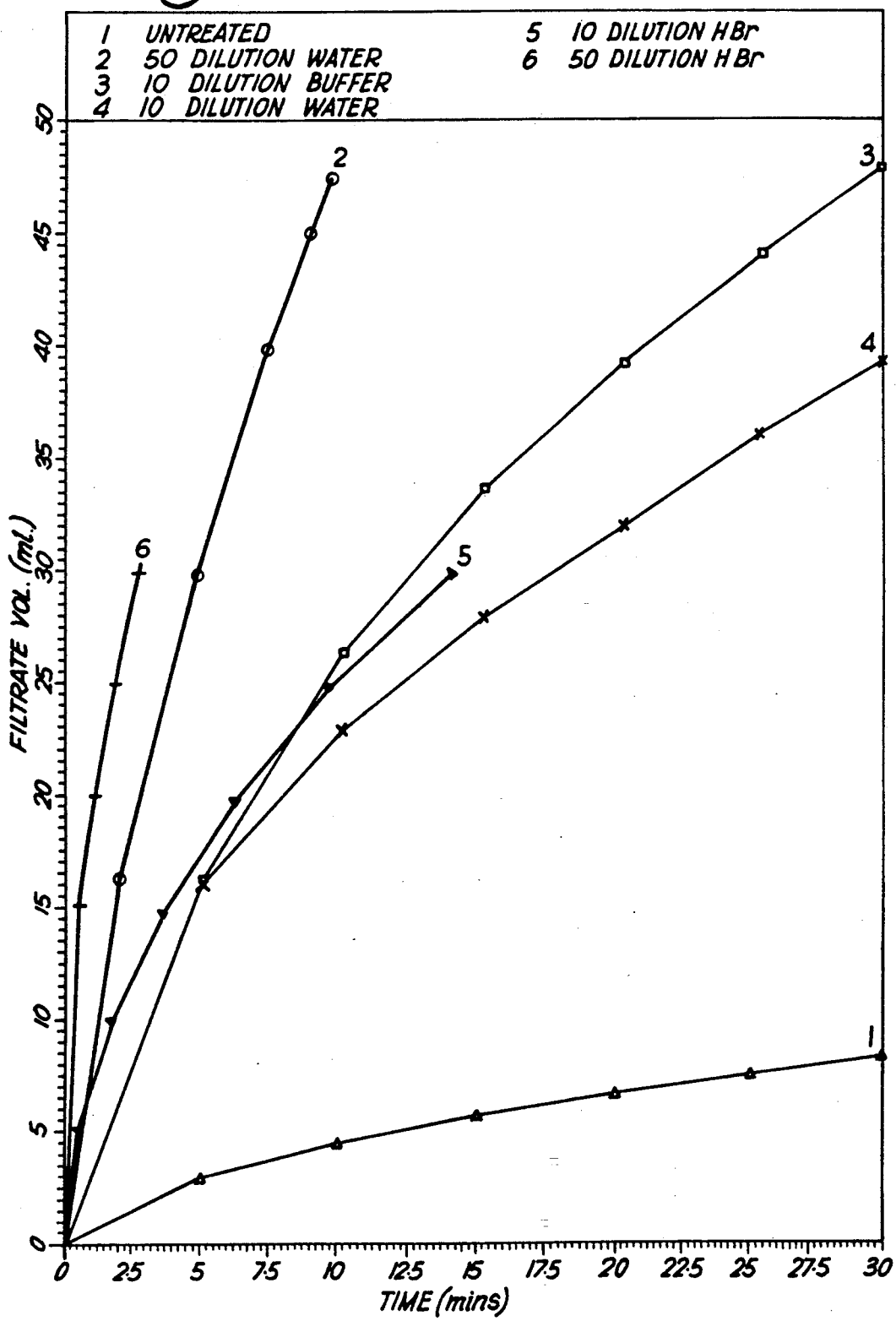
FIG. 2 is a graph showing filtrate volume vs. time for different treatments.

The filtration results are shown in FIG. 2 of the accompanying Drawings; Line 5 shows the 10-times results, Line 6 the 50-times ones. It will be clear that acidification and dilution together greatly improved the filtrability of the mud samples—and that the combination was a considerable advance over dilution (with water) alone.

The ion chromatography results were as follows:

| Ion | Molar Concentration ($\times 10^{-3}$) | | |
|---|---|---|---|
| | actual | 10 times | 50 times |
| $Na^+$ | 17.7 | NM | NM |
| $Ca^{++}$ | 100. | NM | 95 |
| $Cl^-$ | 5.4 | NM | NM |
| $SO_4^{--}$ | 3.9 | NM | NM |
| $CO_3^{--}$ | 102. | NM | 56 |

From these results it is clear that even at as little as 50-times dilution the use of acid to reduce the pH is successful at dissolving the calcium carbonate, although in the open (rather than closed) system employed here the dissolved carbonate was largely converted to gaseous carbon dioxide, and lost from the system. Performing the acidification is a closed vessel, and subsequently raising the pH again, "traps" the carbon dioxide, and gives a better result.

EXAMPLE 3: DETERMINATION OF CEC

A freshwater mud (A) was formulated with the following composition:
2.5 liters deionised water
0.01 g sodium hydroxide (conc.=$1 \times 10^{-4}$ molar)
0.731 g sodium chloride (conc.=$5 \times 10^{-3}$ molar)
2.02 g sodium sulphate (conc.=$2.5 \times 10^{-3}$ molar)
25.00 g calcium carbonate
192.5 g bentonite
980.0 g barite The above formulation gives:
total mud volume=2.820 liters
measured pH=9.80
solids content=32.20 weight percent
mud density=1310 kg/m$^3$
API fluid loss=11.75 ml A second freshwater mud (B) was formulated with the same concentrations of all components as mud (A) but without sodium chloride and sodium sulphate. API filtrates of both muds (A) and (B) were analysed by ion chromatography and the results shown in Table 1. The differences between the ion concentrations in filtrate (A) and filtrate (B) are due to the added sodium, sulphate and chloride ions. Excellent agreement is seen between the measured differences in ion concentrations and the added salt concentrations. Ions measured in the filtrate of the mud (B) originate from the added mud solids. All of the carbonate found in the mud filtrates (A) and (B) originate from the impurity salts in the bentonite. Very little of the added calcite is soluble in either mud and therefore does not appear in the mud filtrate. The estimated sodium carbonate content of the bentonite is 2.11%.

The ionic content of the mud (A) and the cation exchange capacity of the mud solids is now determined by the whole mud analysis technique. One ml of mud (A) is removed from the bulk mud and added to known volume of a tetraethylammonium bromide solution of a known concentration. The addition of the quaternary ammonium salt both ion exchanges the clays in the mud solids and flocculates the solids to facilitate solid-liquid separation. The reaction mixture was diluted by the addition of a known volume of water, mixed thoroughly and filtered using a low pressure filtration method, e.g., a syringe filter. The filtrate was then analysed by ion chromatography. In addition to the calibrations needed for each ion analysed by the ion chromatograph, a separate calibration curve was constructed for the tetraethylammonium ion consisting of a plot of peak areas as a function of known ion concentration. The decrease in the concentration of tetraethylammonium ion in the filtrate gives a direct measure of the cation exchange capacity of the mud solids.

The results are summarised in Table 2 which shows the measured uptake of tetraethylammonium ion and the measured concentration of all of the ions in the filtrate, including the ions released by the cation exchange process. The measured uptake of tetraethylammonium ion was 0.05 moles per liter of mud compared to a release of sodium of 0.055 moles per liter of mud which corresponds to the Na$^+$ content in the whole mud (A) filtrate (Table 2) minus the Na$^+$ content in mud filtrate (A) (Table 1). The removal of tetraethylammonium ions from the filtrate has been compensated by the release of sodium ions into the filtrate.

From the measured uptake of tetraethylammonium ion the CEC of the mud solids can be calculated. The CEC of the mud solids is therefore 0.05 moles per liter of mud or 50 milliequivalents (meq) per liter of mud. The solids content of the mud is 32.2 weight percent or 422 grams per liter of mud or 0.422 g per ml of mud; the CEC per unit weight of solids is therefore $$CEC = \frac{5.0 \times 10^{-5}}{0.422} \text{ moles/g} = 0.12 \text{ meq/g} \quad (11)$$

Clearly the CEC of the mud solids is due only to the presence of bentonite (68.2 gram per liter of mud); the CEC of the bentonite is therefore $$Bentonite CEC = \frac{5.0 \times 10^{-5}}{0.068} \text{ moles/g} = 0.73 \text{ meq/g} \quad (12)$$

which is within the range 0.7-0.8 meg/g usually found for commercial bentonites. Another useful calculation is to use the measured CEC of the mud solids to calculate the bentonite content from the known value of the CEC of the bentonite.

TABLE 1

ION ANALYSIS OF API FILTRATE

ION CONCENTRATION (moles/l of mud)

| ION | FRESHWATER MUD FILTRATE (A) | FILTRATE (B) | DIFFERENCE (A) − (B) |
|---|---|---|---|
| Na$^+$ | $4.73 \times 10^{-2}$ | $3.64 \times 10^{-2}$ | $1.09 \times 10^{-2}$ |
| K$^+$ | $1.6 \times 10^{-4}$ | $1.5 \times 10^{-4}$ | $1 \times 10^{-5}$ |
| Mg$^{2+}$ | 0 | 0 | 0 |
| Ca$^{2+}$ | $1.2 \times 10^{-4}$ | $1.1 \times 10^{-4}$ | $1.1 \times 10^{-5}$ |
| Cl$^-$ | $1.08 \times 10^{-2}$ | $5.4 \times 10^{-3}$ | $5.4 \times 10^{-3}$ |
| SO$_4^{2-}$ | $4.8 \times 10^{-3}$ | $2 \times 10^{-3}$ | $2.7 \times 10^{-3}$ |
| CO$_3^{2-}$ | $1.37 \times 10^{-2}$ | $1.36 \times 10^{-2}$ | $1 \times 10^{-4}$ |

TABLE 2

IONS ANALYSIS OF WHOLE MUD (A) FILTRATE

| ION | CONC (moles/l of mud) |
|---|---|
| TETRAETHYLAMMONIUM | $5.0 \times 10^{-2}$ (taken up) |
| Na$^+$ | 0.1023 |
| K$^+$ | 0 (too low to measure) |
| Ca$^{2+}$ | $2.8 \times 10^{-4}$ |
| Mg$^{2+}$ | 0 (too low to measure) |
| Cl$^-$ | $9.1 \times 10^{-3}$ |
| SO$_4^{2-}$ | $4.5 \times 10^{-3}$ |
| CO$_3^{2-}$ | $1.58 \times 10^{-2}$ |

We claim:
1. A method for determining the ionic components in a drilling mud, said method comprising the steps of:
   a) removing from said drilling mud a sample to be analysed;
   b) treating said sample by reducing the pH thereof so as to flocculate clay components thereof and to solubilize undissolved active materials therein;
   c) separating solid and liquid parts of the treated sample; and
   d) using an ion chromatographic technique to analyse said liquid part to determine the ionic content thereof.

2. A method as claimed in claim 1, wherein said drilling mud contains one or more components selected from the group consisting of: viscosifiers, dispersants, pH controllers, calcium controllers and density regulants.

3. A method as claimed in claim 1, in which said sample is taken just after said drilling mud leaves a well bore.

4. A method as claimed in claim 1, in which the treating step comprises adding an acid to said sample.

5. A method as claimed in claim 4, in which the acid is a mineral acid.

6. A method as claimed in claim 5, in which the acid is hydrobromic acid.

7. A method as claimed in claim 4, further comprising adding an amount of acid sufficient to cause the mud sample's pH to be reduced to from about 6 to about 8.

8. A method as claimed in claim 1, further comprising adding a flocculant to said sample.

9. A method as claimed in claim 8, in which said flocculant comprises a quaternary ammonium compound.

10. A method as claimed in claim 9, in which the quaternary ammonium compound is tetramethylammonium bromide.

11. A method as claimed in claim 1, further comprising using the determined ionic content as a basis for a calculation of components that were in said sample at ambient conditions extant when and where it was taken.

12. A method as claimed in claim 11, in which said calculation is performed by using a computer programmed to simulate a thermodynamically and chemically accurate model of any reactions involved.

13. A method as claimed in claim 1, wherein said sample is taken just before said drilling mud is returned to a well bore.

14. A method as claimed in claim 1, in which the treating step comprises adding a buffer to said sample.

15. A method as claimed in claim 14, in which the buffer is a quaternary ammonium buffer.

16. A method as claimed in claim 14, in which the amount of buffer added to said sample is sufficient to reduce the pH of said sample to from about 8 to about 9.

17. A method as claimed in claim 1, further comprising the steps of adding an excess quantity of a displacement agent to said sample prior to said step of separating solid and liquid parts such that cations carried by mud solids are displaced into solution and are subsequently separated off with said liquid part; and determining a remaining quantity of said displacement agent in said liquid part in order to determine how much of said excess has been consumed by said mud solids, thereby obtaining an indication of the cation exchange capacity of said mud solids.

18. A method as claimed in claim 17, further comprising the steps of determining equilibrium constants for all reactions known to occur between primary components of the mud; constructing mass balance equations for said primary components; and solving said equations for each species concentration.

19. A method as claimed in claim 17, further comprising using the determined ionic content as a basis for the calculation of components that were in said sample at ambient conditions extant when and where it was taken.

20. A method as claimed in claim 19, further comprising performing said calculation using a computer programmed to simulate a thermodynamically and chemically accurate model of any reactions involved.

21. A method for determining the ionic components in a drilling mud, said method comprising the steps of:
a) removing from said drilling mud a sample to be analysed;
b) adding an excess quantity of a displacement agent to said sample so as to displace substantially all cations from mud solids into solution;
c) separating solid and liquid parts of the sample;
d) analysing the ionic content of said liquid part by an ion chromatographic technique so as to determine the amount of displacement agent not taken up by the mud solids; and
e) calculating the cation exchange capacity of the mud solids from the results of said analysing step.

22. A method as claimed in claim 21, further comprising treating the sample by reducing the pH thereof to flocculate the mud solids prior to separating the solid and liquid parts of the sample.

23. A method as claimed in claim 21, further comprising the steps of determining equilibrium constants for all reactions known to occur between primary components of the mud; constructing mass balance equations for said primary components; and solving said equations for each species concentration.

24. A method as claimed in claim 1, further comprising the steps of determining equilibrium constants for all reactions known to occur between primary components of the mud; constructing mass balance equations for said primary components; and solving said equations for each species concentration.

25. A method for determining the ionic components in a drilling mud, said method comprising the steps of:
a) removing from said drilling mud a sample to be analysed;
b) adding an excess quantity of a displacement agent comprising tetramethylammonium bromide to said sample such that cations carried by mud solids are displaced into solution;
c) treating said sample by reducing the pH thereof so as to flocculate clay components thereof and to solublize undissolved active materials therein;
d) separating solid and liquid parts of the treated sample;
e) analysing said liquid part to determine the ionic content thereof; and
f) determining a remaining quantity of said displacement agent in said liquid part in order to determine how much of said excess has been consumed by said mud solids, thereby obtaining an indication of the cation exchange capacity of said mud solids.

26. A method for determining the ionic components in a drilling mud, said method comprising the steps of:
a) removing from said drilling mud a sample to be analysed;
b) treating said sample by reducing the pH thereof by adding a quaternary ammonium buffer comprising tri(hydroxymethyl)aminomethane so as to flocculate clay components thereof and to solublize undissolved active materials therein;
c) separating solid and liquid parts of the treated sample; and
d) analysing said liquid part to determine the ionic content thereof.

* * * * *